United States Patent
Wu et al.

(10) Patent No.: US 6,727,287 B2
(45) Date of Patent: Apr. 27, 2004

(54) TOLUENE SULFONAMIDE-CONTAINING ANTI-TUMOR COMPOSITION AND METHOD OF USE THEREOF

(75) Inventors: John Y. J. Wu, Lloyd Neck, NY (US); Rocky C. S. Shih, San Antonio, TX (US); Lester J. Wu, Lloyd Neck, NY (US)

(73) Assignee: PTS International, Inc., San Antonio, TX (US)

( * ) Notice: Subject to any disclaimer, the term of this patent is extended or adjusted under 35 U.S.C. 154(b) by 0 days.

(21) Appl. No.: 09/835,908

(22) Filed: Apr. 16, 2001

(65) Prior Publication Data

US 2003/0022843 A1 Jan. 30, 2003

(51) Int. Cl.$^7$ .............................................. A61K 31/18
(52) U.S. Cl. ....................................... 514/604; 424/423
(58) Field of Search .......................... 514/604; 424/423

(56) References Cited

U.S. PATENT DOCUMENTS

| | | |
|---|---|---|
| 3,340,148 A | 9/1967 | Pugh |
| 4,160,452 A | 7/1979 | Theeuwes |
| 4,256,108 A | 3/1981 | Theeuwes |
| 4,265,874 A | 5/1981 | Bonsen et al. |
| 4,663,308 A | 5/1987 | Saffran et al. |
| 4,777,049 A | 10/1988 | Magruder et al. |
| 4,885,174 A | 12/1989 | Bodor et al. |
| 4,983,396 A | 1/1991 | Bodor et al. |
| 5,891,454 A | 4/1999 | Wu |

FOREIGN PATENT DOCUMENTS

| | | |
|---|---|---|
| CN | 1204511 A | 1/1999 |
| GB | 11269 A1 | 8/1989 |

Primary Examiner—James H. Reamer
(74) Attorney, Agent, or Firm—Akin Gump Strauss Hauer & Feld LLP

(57) ABSTRACT

The invention relates to compositions which exhibit anti-tumor activity and which comprise a toluene sulfonamide at a concentration not previously recognized as being efficacious for this purpose. The compositions exhibit the ability to inhibit tumor growth, shrink (i.e., necrotize) tumors, and prevent tumor formation in humans. The invention also includes methods of making and using the compositions.

28 Claims, 5 Drawing Sheets

US 6,727,287 B2

TOLUENE SULFONAMIDE-CONTAINING ANTI-TUMOR COMPOSITION AND METHOD OF USE THEREOF

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

Toluene sulfonamide is known to be a highly effective anti-fungal agent, and is useful for treating plant and animal (e.g., human) tissues infected with a fungus. For instance, U.S. Pat. No. 3,340,148 to Pugh discloses that para-toluene sulfonamide is highly effective as a topical agent for treatment of fungal skin diseases.

U.S. Pat. No. 5,981,454 to Wu discloses a toluene sulfonamide-containing composition that exhibits anti-cancer and tumor necrotizing activity. That patent discloses that the minimum effective concentration of toluene sulfonamide in such a composition is 10% by weight. The present invention relates to efficacious anti-cancer compositions that were not previously described by others.

BRIEF SUMMARY OF THE INVENTION

The invention relates to a pharmaceutical composition that exhibits anti-tumor activity. The composition comprises less than 10%, by weight, (or less than 9%, 7%, 3%, or 1%) of a toluene sulfonamide and a pharmaceutically acceptable carrier. The carrier can, for example, be an injectable carrier or an orally-administrable carrier. The precise identity of the toluene sulfonamide is not critical. The sulfonamide moiety can be in the meta-, ortho-, or para- position, and the nitrogen atom can be substituted with two hydride radicals. One or both of the hydride radicals can be replaced by a $C_1$ to $C_6$ straight, branched, or cyclic organic radical. Examples of suitable toluene sulfonamides include para-toluene sulfonamide, ortho-toluene sulfonamide, meta-toluene sulfonamide, N-ethyl ortho-toluene sulfonamide, N-ethyl para-toluene sulfonamide, and N-cyclohexyl para-toluene sulfonamide. The composition can comprise two or more toluene sulfonamides.

The pharmaceutically acceptable carrier comprises one or more additional ingredients. Suitable ingredients include 0–90% (w/w) polyethylene glycol, 0–90% (w/w) 2-ethyl-1, 3-hexanediol, 0–90% (w/w) propanediol, 0–50% (w/w) decanedioic acid, 0–25% (w/w) dimethyl sulfoxide, 0–50% (w/w) ethanol, honey, a surfactant, and an emulsifier.

The invention also includes a method of making the pharmaceutical composition exhibiting anti-tumor activity. The method comprises combining a toluene sulfonamide and a pharmaceutically acceptable carrier to form the composition.

In another aspect, the invention relates to a method of inhibiting growth of a tumor in a human patient. This method comprises administering to the patient the pharmaceutical composition described herein, i.e., one comprising less than 10%, by weight, of a toluene sulfonamide. Administration of the composition to the patient inhibits growth of the tumor. The composition can be orally administered to the patient, infused into a blood vessel of the patient, injected at a tumor site in the patient, or topically applied at a tumor site.

The pharmaceutical composition described herein can also be used to shrink a tumor in a human patient who has a tumor, or to prevent tumorigenesis in a human patient who does not have, or is not recognized as having, a tumor.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. The invention is not limited to the precise arrangements and instrumentalities shown in the drawings.

DETAILED DESCRIPTION OF THE INVENTION

Figures 1A, 1B:
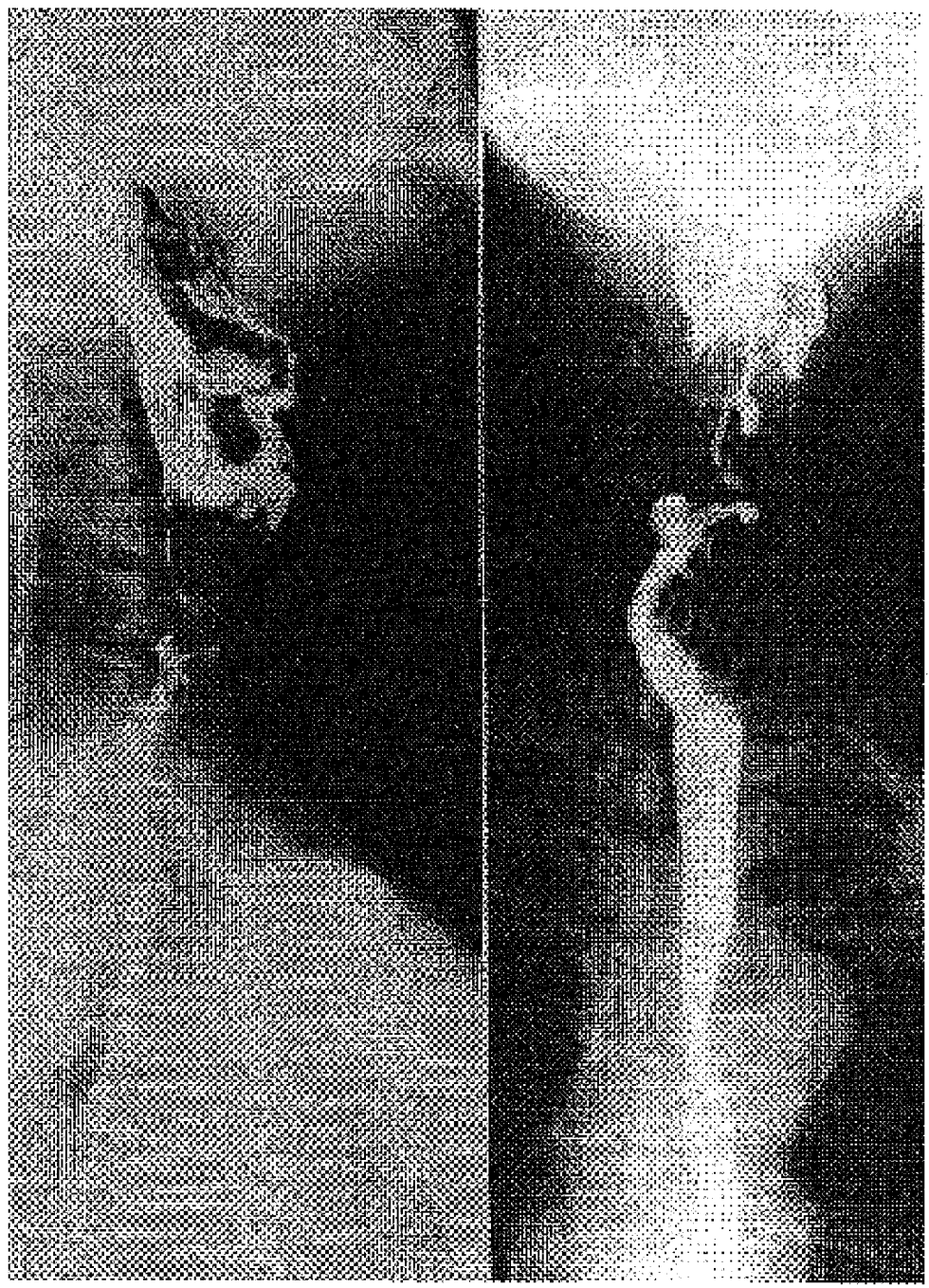
FIG. 1, consisting of FIGS. 1A and 1B is a pair of radiographic images of the narrowed esophageal lumen of the patient referred to herein as Patient 1. The images were made during consumption by Patient 1 of a barium-containing meal, and indicate that the upper portion of the patient's esophagus was narrowed along 8 to 9 centimeters of its length by the cauliflower-like mass observed therein. The images shown in FIGS. 1A and 1B were made prior to commencing administration of a toluene sulfonamide-containing composition described herein.

One of the inventors previously disclosed (i.e., in U.S. Pat. No. 5,891,454) that toluene sulfonamides are efficacious anti-tumor agents, at least in specialized compositions. However, it was believed that 10%, by weight, was the minimum content of toluene sulfonamide that could be used to make an efficacious pharmaceutical composition. In the present invention, the inventors have discovered that efficacious anti-tumor compositions can contain less than 10%, by weight, of a toluene sulfonamide.

Anti-Tumor Pharmaceutical Compositions

The invention includes a pharmaceutical composition that exhibits anti-tumor activity, including tumor growth-inhibiting activity, tumor-shrinking (necrotizing) activity, and tumor-preventive activity. The composition comprises a toluene sulfonamide at a concentration of less than 10%, by weight, of the composition. The composition also comprises a pharmaceutically acceptable carrier. In certain embodiments, the carrier is preferably either an injectable (or infusible) carrier or an orally-administrable (i.e., swallowable, chewable, or edible) carrier. The pharmaceutical composition can contain other ingredients as well, such as are known in the art or described elsewhere in this disclosure.

One advantage of toluene sulfonamides is that they are generally relatively harmless to non-cancerous cells and tissues, even when administered in large amounts or in relatively high concentration. For example, normal (i.e., non-neoplastic) cells exhibit almost no histopathological changes when exposed to para-toluene sulfonamide. Toluene sulfonamides are highly toxic to neoplastic cells, however, and the efficacy of these compounds for anti-cancer purposes relates to this toxicity.

The toluene sulfonamide has the following general formula, wherein the floating bond between the sulfur atom and the toluene moiety indicates that the sulfonamide moiety can be present at any one of the meta-, ortho-, and para-positions.

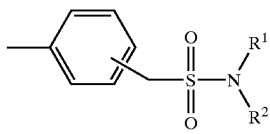

wherein each of $R^1$ and $R^2$ is —H, or a $C_1$ to $C_6$ linear, branched, or cyclic moiety.

The toluene sulfonamide is a toluene molecule substituted, at either the ortho- or para-position with a sulfonamide moiety. The nitrogen atom of the sulfonamide moiety can have a lower alkyl or cycloalkyl moiety (i.e., a $C_1$ to $C_6$ linear, branched, or cyclic moiety) bound thereto. Examples of toluene sulfonamides include para-toluene sulfonamide (i.e., the sulfonamide moiety is at the para- position and each of $R^1$ and $R^2$ is —H), ortho-toluene sulfonamide, N-ethyl ortho-toluene sulfonamide (i.e., $R^1$ is an ethyl radical and $R^2$ is —H), N-ethyl para-toluene sulfonamide, and N-cyclohexyl para-toluene sulfonamide (i.e., $R^1$ is a cyclohexyl {—$C_6H_{11}$} radical and $R^2$ is —H). Other useful toluene sulfonamides can be identified simply by confirming their efficacy using the tests described in this disclosure.

The pharmaceutical composition can comprise more than one toluene sulfonamide. When the composition includes more than one toluene sulfonamide, the sum of the concentrations of the individual toluene sulfonamides is preferably less than 10%, by weight, of the composition.

The precise amount of the toluene sulfonamide(s) present in the pharmaceutical composition is not critical, other than that the total content of toluene sulfonamides should be less than 10%, by weight, of the composition. In certain embodiments, the total content is less than 10%, 9%, 8%, 7%, 5%, 3%, 1%, 0.5%, or 0.1%, by weight, of the composition. The toluene sulfonamide content of the composition can be as low as necessary in order to preserve the palatability of an orally-administered pharmaceutical composition. Nevertheless, the concentration of toluene sulfonamide in an orally-administered pharmaceutical composition should be maintained at the highest level (less than 10%) that preserves palatability of the composition, so that the efficacy of the composition can be maximized. If the composition is anticipated to be readily consumable in large (e.g., multi-gram or multi-decagram) amounts, then, of course, the absolute concentration of the toluene sulfonamide in the composition is less critical, owing to the amount of the composition that can be administered to a patient.

Other contemplated ingredients of the pharmaceutical composition include, for example, polyethylene glycol, 2-ethyl-1,3-hexanediol, propanediol, decanedioic acid, dimethyl sulfoxide, ethanol, honey, a surfactant (i.e., other than, or in addition to, honey), and an emulsifier. Examples of suitable surfactants include honey, hexadecanol, propanediol alginate, glycerol monostearate, and xylitan monostearate. Examples of suitable emulsifiers include hexadecanol, TWEEN™ surfactants (e.g., TWEEN20™), lecithin, and other known emulsifying agents.

The invention encompasses the preparation and use of medicaments and pharmaceutical compositions comprising less than 10%, by weight, of a toluene sulfonamide as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. Administration of one of these pharmaceutical compositions to a subject is useful for inhibiting tumor growth, for shrinking tumors, and for preventing tumorigenesis in the human subjects, as described elsewhere in the present disclosure. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition and which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, nasal, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. A unit dose of a pharmaceutical composition of the invention will generally comprise from about 100 milligrams to about 10 grams of the active ingredient.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Oral compositions may be made, using known technology, which specifically release orally-administered agents in the small or large intestines, esophagus, or stomach of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273–280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984, J. Med. Chem. 27:261–268) and a variety of naturally available and modified polysaccharides (PCT GB 89/00581) may be used in such formulations.

Pulsed release technology such as that described in U.S. Pat. No. 4,777,049 may also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous, viscous, or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may farther comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules, in multi-dose containers containing a preservative, or in single-use devices for auto-injection or injection by a medical practitioner. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and sprayable solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 10% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets (e.g., an inhalable mist) of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 10% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

It is understood that the ordinarily skilled physician or oncologist will readily determine and prescribe an effective amount of the compound to inhibit tumor growth, induce tumor shrinkage, or inhibit or prevent tumorigenesis in the subject. In so proceeding, the physician or oncologist may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the stage or severity of any existing tumor.

Another aspect of the invention relates to a kit comprising a pharmaceutical composition of the invention and an instructional material. As used herein, an "instructional material" includes a publication, a recording, a diagram, or any other medium of expression which is used to communicate the usefulness of the pharmaceutical composition comprising less than 10%, by weight, of a toluene sulfonamide for inhibiting tumor growth, inducing tumor shrinkage, or inhibiting or preventing tumorigenesis in a human subject. The instructional material may also, for example, describe an appropriate dose of the pharmaceutical composition of the invention. The instructional material of the kit of the invention may, for example, be affixed to a container which contains a pharmaceutical composition of the invention or be shipped together with a container which contains the pharmaceutical composition. Alternatively, the instructional material may be shipped separately from the container with the intention that the instructional material and the pharmaceutical composition be used cooperatively by the recipient.

The invention also includes a kit comprising a pharmaceutical composition of the invention and a delivery device for delivering the composition to a subject. By way of example, the delivery device may be a squeezable spray bottle, a metered-dose spray bottle, an aerosol spray device, an atomizer, a dry powder delivery device, a self-propelling solvent/powder-dispensing device, a syringe, a needle, a tampon, or a dosage measuring container. The kit may further comprise an instructional material as described herein.

In one embodiment, the pharmaceutical composition has the composition set forth in Table 1.

TABLE 1

| Ingredient | Concentration (%, by weight, of the composition) |
| --- | --- |
| Para-toluene sulfonamide | 6.00 |
| Polyethylene glycol | 6.70 |
| 2-Ethyl-1,3-hexanediol | 3.28 |
| Propanediol | 1.64 |
| Decanedioic acid | 0.74 |
| Dimethyl sulfoxide | 1.34 |
| Ethanol | 0.30 |
| Honey | 80.00 |

In another embodiment, the pharmaceutical composition is formulated to be an ingestible food or beverage product comprising a relatively low amount (e.g., 9.9%, 6%, 3%, 1%, 0.5%, or 0.1% or less, by weight, of the product) of a toluene sulfonamide. Such compositions are useful for preventing tumor formation in humans at risk for tumorigenesis.

These products can be used both by humans who have never been afflicted with a tumor and by humans who have previously been afflicted with a tumor (i.e., in order to prevent recurrence of the same tumor or formation of another tumor). In one embodiment, the product is a normal foodstuff (e.g., a tea or a biscuit) that has been supplemented with a toluene sulfonamide. In another embodiment, the product is a liquid, solid, or semi-solid that is not a normal foodstuff, but has been formulated for use as a tumor preventive agent. Semi-solid or liquid formulations are preferred for humans who have difficulty swallowing or retaining solid foods.

Anti-Tumor Methods

The invention includes methods of inhibiting tumor growth, shrinking tumors, and preventing tumor formation (i.e., tumorigenesis) in a human. Each of these methods involves administering a toluene sulfonamide-containing pharmaceutical composition described herein to a human who is either already afflicted with a tumor or at risk for developing a tumor. The method of administering the composition is not critical. For example, the compositions can be administered orally, rectally, topically, parenterally, by infusion, or by a pulmonary route. For certain types of tumors, particular routes of administration can be preferred. For example, in humans afflicted with a tumor in a tissue lining a body cavity (e.g., lung, esophageal, and gastric tumors of epithelial origin), administration of a viscous or adhesive composition to the body cavity, and preferably to the lining of the cavity, is preferred. The viscous composition is more viscous than water at body temperature, and is preferably more viscous than body fluids that are normally present at the tissue lining the cavity. The adhesive composition comprises an agent which is not easily rinsed from the tissue lining the cavity by normal body fluids. The net effect of administering the viscous or adhesive composition is that the toluene sulfonamide is localized at or near the site of a tumor or of potential tumorigenesis. In another embodiment, a injectable form of a pharmaceutical composition described herein is injected at or near a tumor site or at or near a body location where tumorigenesis is suspected.

EXAMPLES

The anti-tumor activities of the pharmaceutical compositions have been demonstrated in in vivo experiments and in limited clinical studies. The results obtained from those experiments and trials demonstrate that pharmaceutical compositions comprising less than 10%, by weight, of a toluene sulfonamide exhibit remarkable anti-tumor activities. These experiments and studies are described with reference to the following Examples. These Examples are provided for the purpose of illustration only and the invention is not limited to these examples, but rather encompasses all variations which are evident as a result of the teaching provided herein.

Example 1

Preparation of a Pharmaceutical Composition Comprising Toluene Sulfonamide

All the chemical ingredients employed to form the composition described in this Example are commercially available. The preparation of the pharmaceutical composition essentially comprised making the composition described in Example 1 of U.S. Pat. No. 5,891,454 and then diluting that composition five-fold with honey. The diluted composition was thoroughly mixed, bottled, and sterilized.

Example 2

In Vivo Anti-Tumor Activity of Pharmaceutical Compositions Comprising Para-Toluene Sulfonamide In this Example, experiments are described in which documented the ability of pharmaceutical compositions to inhibit growth of tumor cells in vivo. The pharmaceutical compositions comprised para-toluene sulfonamide in various concentrations.

Mice harboring transplanted tumor cells were used as an in vivo model of tumor growth. Hepatocarcinoma cells were implanted into a first group of selected mice. Sarcoma S-180 cells were implanted into a second group of selected mice. The average weight of the mice used was 20 grams A pharmaceutical composition was prepared as described in Example 1 and diluted in a solution comprising physiological saline and 5% (v/v) TWEEN20™ to form individual pharmaceutical compositions which comprised para-toluene sulfonamide (PTS) at concentrations of 10.8%, 5.8%, and 4.1%, by weight. Individual mice received 0.2 milliliters of one of these pharmaceutical compositions each day for ten consecutive days by gavage. As a control ("Control 1" in the tables below), selected mice received the saline/TWEEN20™ solution that did not contain any PTS for 10 consecutive days by gavage. As a further control ("Control 2" in the tables below), selected mice were not administered PTS or the saline/TWEEN20™ solution by gavage. The 10-day treatment regimen was then repeated, for a total of 20 days of treatment.

Twenty days following the beginning of administration of the selected composition, the mice were humanely sacrificed, and the weight of the tumor mass was determined and compared with the weight of the tumor cells that were initially implanted. Inhibition of tumor growth was assessed by comparing tumor growth in mice to Control 2 mice. The results obtained in these experiments are shown in Table 2 (corresponding to experiments using transplanted hepatocarcinoma cells) and Table 3 (corresponding to experiments using transplanted sarcoma S-180 cells). P values were calculated using statistical methods.

TABLE 2

| Composition | [PTS] (% by weight) | Percent Inhibition of Tumor Growth Rate (in 3 separate experiments) | | | P value |
| --- | --- | --- | --- | --- | --- |
| 1 | 4.1 | 45.9 | 41.3 | 30.0 | <0.01 |
| 2 | 5.8 | 41.9 | 44.6 | 41.2 | <0.01 |
| 3 | 10.8 | 50.7 | 49.3 | 47.9 | <0.01 |
| Control 1 | 0 | −2.5 | 1.9 | −2.7 | <0.05 |
| Control 2 | 0 | — | — | — | — |

TABLE 3

| Composition | [PTS] (% by weight) | Percent Inhibition of Tumor Growth Rate (in 3 separate experiments) | | | P value |
| --- | --- | --- | --- | --- | --- |
| 1 | 4.1 | 36.3 | 31.3 | 33.8 | <0.01 |
| 2 | 5.8 | 47.9 | 43.5 | 46.1 | <0.01 |
| 3 | 10.8 | 53.7 | 49.3 | 51.3 | <0.01 |
| Control 1 | 0 | — | — | — | — |
| Control 2 | 0 | — | — | — | — |

The results of these experiments demonstrate that pharmaceutical composition that comprise less than 10%, by weight, of a toluene sulfonamide exhibit tumor growth-activity, and can be expected to exhibit the other tumor-shrinking and tumor-preventing activities.

Example 3

Limited Human Clinical Trials of a Pharmaceutical Composition Comprising 6% Para-Toluene Sulfonamide The human clinical data presented in this Example demonstrates that oral administration of pharmaceutical composition comprising 6%, by weight, para-toluene sulfonamide (PTS) effectively inhibits esophageal cancer in humans.

The pharmaceutical composition was made as described in Example 1, except that the concentration of PTS in the composition was 30% prior to dilution, and therefore 6.0% (i.e., after five-fold dilution with honey) in the syrup administered to the patients. Patients were advised to swallow the syrup slowly, and not to drink any other liquid for half an hour. Owing to the bitterness of the syrup, the composition was provided in a 10 or 20 milliliter syringe (without needle), which allowed delivery of the composition to the patient's throat, and minimization of contact of the syrup with the patient's tongue. The composition was administered twice per day, for a period of at least two or three weeks, and daily administration continued for years in some instances.

The treatment has been tested in treating more than a dozen patients afflicted with late stage esophageal cancer, and therapeutic effect has been demonstrated in about 75% of the patients treated. Esophageal cancer patients frequently have difficulty swallowing. For many patients treated with the composition, swallowing difficulties were relieved within two or three weeks following the onset of treatment. The treatment can be administered after or during chemotherapy, radiotherapy, or both, and enhances the therapeutic effectiveness of those interventions. The toluene sulfonamide treatment also prolongs the utility of the trans-esophageal self-expanding metallic stent that has been described by others. As examples of the therapeutic effectiveness that can be achieved by administration of a composition comprising less than 10%, by weight, toluene sulfonamide, the following two case studies are provided.

Case Study 1

Patient 1 was a 62-year-old female afflicted with late stage esophageal cancer, who had complained of dysphagia for about one year prior to treatment. Around the time PTS administration was begun, Patient 1 experienced difficulty swallowing, was on semi-liquid diet, and had been diagnosed with squamous cell carcinoma of upper cervical esophagus. Radiographic imaging of the patient during ingestion of a barium-containing meal demonstrated that the patient's esophageal lumen was narrow and irregular along about 9 centimeters of its length (See FIG. 1).

Figure 2:
FIG. 2 is a radiographic image of the upper portion of the esophagus of Patient 1 about 43 months after beginning administration of a para-toluene sulfonamide-containing composition described herein. The image was made during ingestion of a barium-containing meal, and indicates the smooth, normal state of the patient's previously obstructed esophagus.

Patient 1 was first treated by direct extension radiation, whereby a total of about 6,000 rads was administered to the tumor site. Severe local irritation occurred, and Patient 1 declined further treatment. As an alternative, the patient was administered the pharmaceutical composition, prepared as described in Example 1 and comprising PTS at a concentration of 6.0% by weight of the composition. The patient was administered 10 milliliters of this composition twice a day (i.e., a daily dose of roughly 1 gram of PTS). After 2 weeks, local symptoms subsided, and the patient was able to swallow some soft food. About one and a half years of this treatment, the dose was reduced to 5 milliliters twice per day (i.e., about 500 milligrams of PTS per day). At this time, the patient could swallow semi-soft diets, reported feeling quite healthy, and started to resume normal house-hold work. About two years thereafter, the patient was able to swallow normally, and the patient's esophagus appeared smooth and normal by radiographic imaging during ingestion of a barium-containing meal (See FIG. 2). At that time, administration of oral liquid composition was discontinued in favor of administration of a soft gel form of the PTS-containing composition (at a dose of about 500 milligrams of PTS per day). About a year later, the therapy was considered no longer necessary and discontinued. So far, the patient has survived more than five years, and recurrence of the tumor has not been detected.

The efficacy of this therapeutic regimen is particularly surprising, in view of the poor outlook of late stage esophageal cancer patients. For late staging esophageal cancer patients treated with conventional chemo- and radiotherapies, the 5-year survival rate is only about 20% (using information provided by the American Cancer Society). Patient 1 did not respond well to traditional radiotherapy, but appears to have manifested a near complete remission, without recurrence, following administration of the pharmaceutical composition described herein.

Case Study 2

Figures 3A, 3B, 3C:
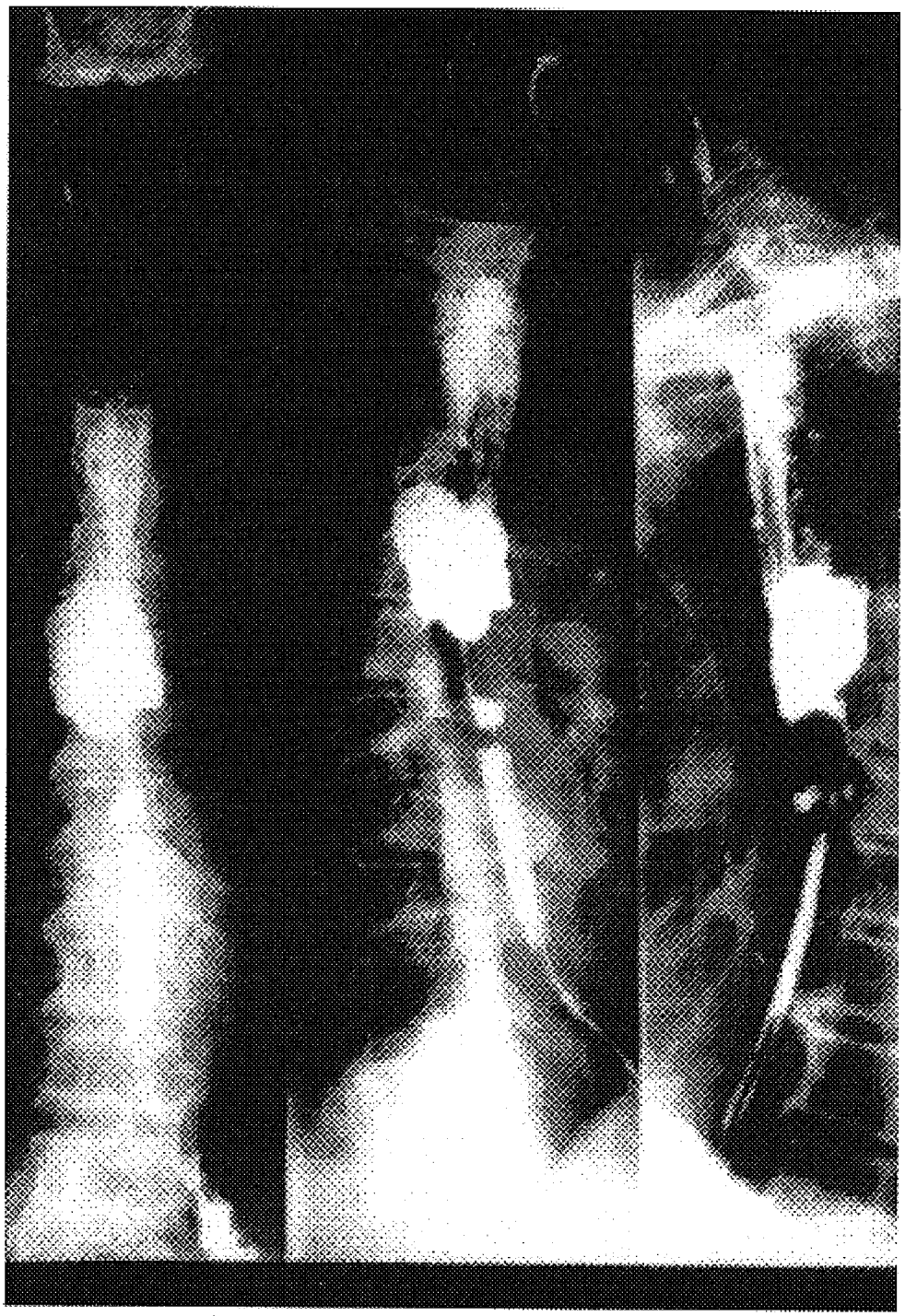
FIG. 3, consisting of FIGS. 3A, 3B, and 3C, is a trio of radiographic images of the upper portion of the esophagus of the patient referred to herein as Patient 2. The images were made during ingestion of a barium-containing meal and indicate that the patient's esophagus was narrowed along about 10 centimeters of its length. These images were made prior to commencing administration of a toluene sulfonamide-containing composition described herein.

Patient 2 was a 72-year-old male who complained of dysphagia for more than 2 years and was able to consume a liquid diet only with difficulty. The patient was diagnosed as being afflicted with carcinoma of the thoracic esophagus, the tumor being located in the middle portion of the esophagus, the afflicted portion of the esophagus being about 10 centimeters in length (See FIG. 3).

Figure 4:
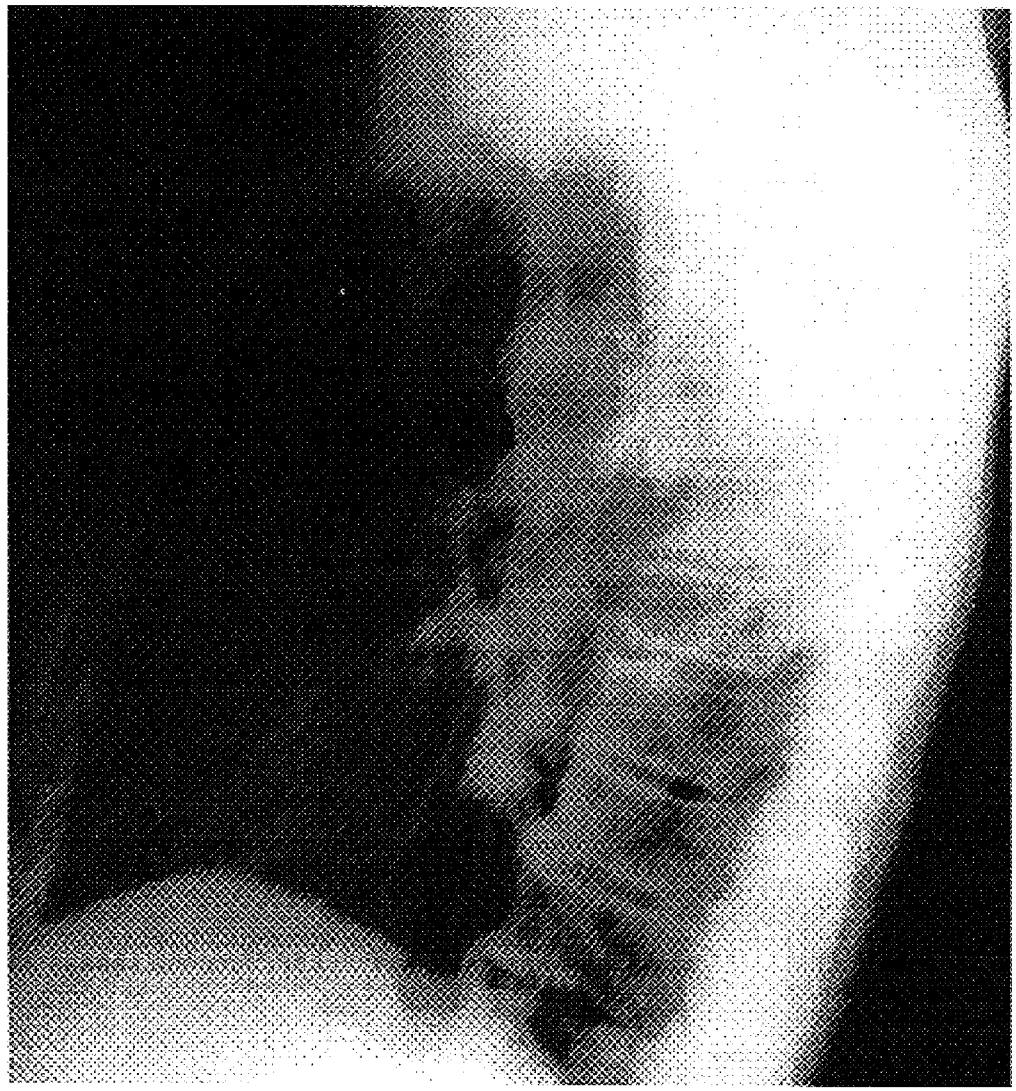
FIG. 4 is a radiographic image of the upper portion of the esophagus of Patient 2 about one week after emplacement of an intra-luminal trans-esophageal stent in the patient's esophagus. Administration of a toluene sulfonamide-containing composition described herein was commenced immediately after emplacing the intra-luminal trans-esophageal stent. The image was made during ingestion of a barium-containing meal, and indicates that esophageal contents could freely pass through the esophagus after the stent had been emplaced, indicating that food and the composition described herein can be administered to the esophagus, including to the cancer-constricted portion.

Because of the patient's debility, a surgical operation was not performed. Because the patient could not swallow at all, a trans-esophageal self-expanding metallic stent was installed under X-ray guidance in order to create a path for swallowing. Emplacement of the stent permitted the patient to swallow soft foods (See FIG. 4).

Figures 5A, 5B:
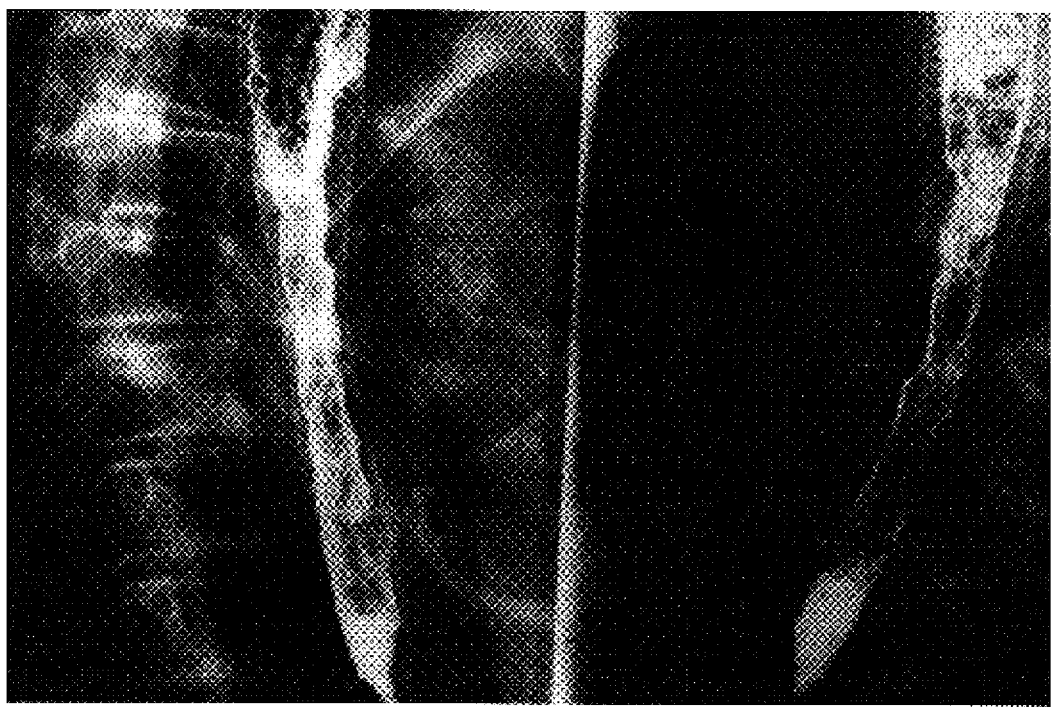
FIG. 5, consisting of FIGS. 5A and 5B, is a pair of radiographic images of the upper portion of the esophagus of Patient 2 about 14 months after beginning administration of a para-toluene sulfonamide-containing composition described herein. The images were made during ingestion of a barium-containing meal, and indicated the smooth, normal passage of a barium-containing meal through the patient's stented esophagus. The image illustrates that the esophageal passage was in good condition, and that the esophageal cancerous growth was suppressed and no longer obstructed the esophagus. Normally, without the treatment as described herein (i.e., by administration of a para-toluene sulfonamide-containing composition), the emplaced stent would be squeezed and narrowed by growth of the esophageal tumor, and the stented passage would be severely obstructed. The results shown in this Figure indicates that the composition containing para-toluene sulfonamide inhibited growth of the cancer in the patient.

Administration of a PTS-containing pharmaceutical composition prepared as described in Example 1 (containing 6.0% PTS, by weight) 3 times per day in aliquots of 6 milliliters (i.e., a total daily dose of about 1.2 grams) was begun immediately upon emplacement of the stent, and has continued for more than fourteen months. During that time, the patient has lived comfortably at home, and has exhibited continuing improvement (See FIG. 5). The patient's bone marrow, liver, and renal functions appear not to have been adversely affected by the treatment.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A pharmaceutical composition exhibiting anti-tumor activity, the composition comprising less than 10%, by weight, of a toluene sulfonamide and a pharmaceutically acceptable aqueous carrier selected from the group consisting of an injectable carrier, an infusible carrier and a palatable, orally-administrable carrier.

2. The pharmaceutical composition of claim 1, wherein the toluene sulfonamide is selected from the group consisting of para-toluene sulfonamide, ortho-toluene sulfonamide, meta-toluene sulfonamide, N-ethyl ortho-toluene sulfonamide, N-ethyl para-toluene sulfonamide, and N-cyclohexyl para-toluene sulfonamide.

3. The pharmaceutical composition of claim 1, comprising at least two toluene sulfonamides.

4. The pharmaceutical composition of claim 3, wherein each toluene sulfonamide is independently selected from the group consisting of para-toluene sulfonamide, ortho-toluene sulfonamide, meta-toluene sulfonamide, N-ethyl ortho-toluene sulfonamide, N-ethyl para-toluene sulfonamide, and N-cyclohexyl para-toluene sulfonamide.

5. The pharmaceutical composition of claim 1, further comprising an additional ingredient selected from the group consisting of polyethylene glycol, 2-ethyl-1,3-hexanediol, propanediol, decanedioic acid, dimethyl sulfoxide, ethanol, honey, a surfactant, and an emulsifier.

6. The pharmaceutical composition of claim 1, wherein the composition comprises up to 90%, by weight, polyethylene glycol.

7. The pharmaceutical composition of claim 1, wherein the composition comprises up to 90%, by weight, 2-ethyl-1,3-hexanediol.

8. The pharmaceutical composition of claim 1, wherein the composition comprises up to 90%, by weight, propanediol.

9. The pharmaceutical composition of claim 1, wherein the composition comprises up to 50%, by weight, decanedioic acid.

10. The pharmaceutical composition of claim 1, wherein the composition comprises up to 25%, by weight, dimethyl sulfoxide.

11. The pharmaceutical composition of claim 1, wherein the composition comprises up to 50%, by weight, ethanol.

12. The pharmaceutical composition of claim 1, wherein the composition comprises para-toluene sulfonamide.

13. The pharmaceutical composition of claim 12, wherein the composition further comprises polyethylene glycol.

14. The pharmaceutical composition of claim 13, wherein the composition further comprises 2-ethyl-1,3-hexanediol.

15. The pharmaceutical composition of claim 1, comprising para-toluene sulfonamide, polyethylene glycol, 2-ethyl-1,3-hexanediol, propanediol, dimethyl sulfoxide, and ethanol.

16. The pharmaceutical composition of claim 15, wherein the composition is palatable and further comprises honey.

17. The pharmaceutical composition of claim 1, comprising less than about 7% by weight of the toluene sulfonamide.

18. The pharmaceutical composition of claim 1, comprising less than about 3% by weight of the toluene sulfonamide.

19. The pharmaceutical composition of claim 1, comprising less than about 1% by weight of the toluene sulfonamide.

20. A method of making a pharmaceutical composition exhibiting anti-tumor activity, the method comprising combining a toluene sulfonamide and a pharmaceutically acceptable aqueous carrier to form the composition, wherein the carrier is selected from the group consisting of an injectable carrier, an infusible carrier and a palatable, orally-administrable carrier, and wherein the composition comprises less than 10% by weight of the toluene sulfonamide.

21. A method of inhibiting growth of a tumor in a human patient, the method comprising administering to the patient an aqueous pharmaceutical composition comprising less than 10%, by weight, of a toluene sulfonamide, thereby inhibiting growth of the tumor.

22. A method of shrinking a tumor in a human patient, the method comprising administering to the patient an aqueous pharmaceutical composition comprising less than 10%, by weight, of a toluene sulfonamide, thereby shrinking the tumor.

23. A method of preventing a tumor in a human patient at risk for developing a tumor, the method comprising administering to the patient an aqueous pharmaceutical composition comprising less than 10%, by weight, of a toluene sulfonamide, thereby preventing development of the tumor.

24. A palatable, aqueous anti-tumor pharmaceutical composition formulated for oral administration to a patient, the composition comprising less than 10%, by weight, of a toluene sulfonamide.

25. The pharmaceutical composition of claim 1, wherein the toluene sulfonamide is ortho-toluene sulfonamide.

26. The method of claim 24, wherein the composition is palatable and administered orally to the patient.

27. The method of claim 26, wherein the composition is in a form selected from the group consisting of a liquid and a syrup.

28. The method of claim 21, wherein the composition is administered by infusion.

* * * * *